United States Patent [19]

Perl et al.

[11] Patent Number: 4,529,419
[45] Date of Patent: Jul. 16, 1985

[54] FILTER FOR GAS FILTRATION

[75] Inventors: Horst Perl; Massoud Karbachsch; Günter Pradel, all of Göttingen; Fritz Reulecke, Adelebsen, all of Fed. Rep. of Germany

[73] Assignee: Sartorius GmbH, Fed. Rep. of Germany

[21] Appl. No.: 605,844

[22] Filed: May 1, 1984

[30] Foreign Application Priority Data

May 3, 1983 [DE] Fed. Rep. of Germany ....... 3316043

[51] Int. Cl.³ ............................................. B01D 53/22
[52] U.S. Cl. ...................................... 55/158; 55/159; 210/436; 210/445
[58] Field of Search .................... 55/55, 158, 159, 189; 210/188, 416.1, 436, 445, 446, 453, 472; 435/287

[56] References Cited

U.S. PATENT DOCUMENTS

| 2,818,178 | 12/1957 | Hodsdon | 210/445 |
| 3,448,011 | 6/1969 | Russomanno | 435/287 |
| 3,471,019 | 10/1969 | Trasen et al. | 210/445 X |
| 3,614,856 | 10/1971 | Sanz et al. | 55/158 X |
| 3,822,601 | 7/1974 | Borom | 55/158 X |
| 3,905,905 | 9/1975 | O'Leary et al. | 55/159 X |
| 3,909,302 | 9/1975 | Mermelstein | 55/158 X |
| 3,929,648 | 12/1975 | Cuthbert | 210/446 X |
| 4,113,627 | 9/1978 | Leason | 210/446 |
| 4,159,954 | 7/1979 | Gangemi | 210/446 |
| 4,170,056 | 10/1979 | Meyst et al. | 210/446 X |
| 4,319,996 | 3/1982 | Vincent et al. | 210/436 X |
| 4,344,777 | 8/1982 | Siposs | 210/436 X |
| 4,404,006 | 9/1983 | Williams et al. | 210/445 X |
| 4,430,213 | 2/1984 | Ishikawa | 210/445 X |
| 4,461,328 | 7/1984 | Kenney | 55/159 X |

Primary Examiner—Robert Spitzer
Attorney, Agent, or Firm—Eric P. Schellin

[57] ABSTRACT

A filter consisting of connected upper housing and lower housing parts and a hydrophobic flat filter disc for gas filtration sandwiched therebetween, intended in particular for an exchange between a container such as a liquid reservoir partially filled with liquid and the surrounding atmosphere. The upper housing part includes an integral channelled filter support having channels for communication into a gas inlet-outlet means of the said upper housing part. The lower housing part includes an integral, channelled filter support having channels for communication into a centrally disposed bore located at a right angle to the filter support and empties into the gas area of a liquid reservoir for instance. The filter support is constructed to prevent liquid from completely blocking the hydrophobic filter disc.

The filter support of the lower housing forms a planar plane with an annular channel therein and a series of radially extending channels terminating at a centrally located bore. The channels having a controlled depth. The bore diameter is also controlled. The upper housing is dimensioned to provide a controlled distance for the filter from the filter support in the lower housing.

6 Claims, 4 Drawing Figures

FILTER FOR GAS FILTRATION

BACKGROUND OF THE INVENTION

The invention concerns a relatively small auxiliary filter. Small filters with a hydrophobic filter membrane are used to aerate and vent closed containers as well as flexible tube and pipe systems which are partially filled with liquid. Such gas filters should make possible a gas exchange between such a container and the ambient surrrounding atmosphere under sterile conditions. The gas volumes to be exchanged are relatively small, so that the filters themselves are small and the circular flat filter blanks have diameters of between about 12 to 100 mm. Such filter units are normally constructed from two plastic facing disc-like housing parts, each of which has an inlet and an outlet and a channeled filter support. The channels provide communicating pathways to the inlet and the outlet. A hydrophobic filter membrane in the form of a flat disc filter is clamped in between annular flanges of the two housing parts so that it is leakproof about its periphery. The two housing parts are adhered or welded on their edges to a unit comparable to the housing part.

The gas filters are either integral into another filter housing in accordance with U.S. Pat. No. 3,448,011, DE-OS No. 1,549,835 and DE-GM No. 8,108,010.7 which filters liquids, or the gas filter is constructed as a separate, attachable unit in acordance with DE-OS No. 3,202,330 which can be connected by means of normal connecting adapters to hose systems or filter units.

A great variety of filter supports have been developed for such small filters, whether they were for filtering liquids or gases, in order to achieve optimum filtration performance. The filter supports which were developed for pure liquid filtration and are equipped with a hydrophilic filter membrane are generally also suitable for the filtration of gases if the filter support is equipped with a hydrophobic filter membrane. Problems only occur if the liquid level of a partially filled liquid reservoir to be aerated or vented momentarily rises to the level of the filter support itself or directly to the level of the hydrophobic membrane and fills up some of the channels of the filter support. This can happen, for example, if the liquid in filter housings in accordance with the state of the art revealed in DE-GM No. 81 08 010.7 and DE-OS No. 1,549,835 gets into the filter support or if the liquid in a closed flexible tube systems filled with medicinal solutions, e.g. infusion solution or blood, rises due to changing pressure conditions in the conduit system to the filter level of the hydrophobic filter. There is a danger in this instance that the hydrophobic membrane becomes blocked and that this brief blockage becomes permanent, since as a consequence of the filter construction the trapped liquid usually can not leave the free spaces of the filter support on account of capillary forces caused by the surface tension of the liquid.

SUMMARY OF THE INVENTION

The invention comprises small filters of the type designed to prevent a blocking of the filter element and to preserve the venting qualities even if the hydrophobic flat filter disc is temporarily and partially wetted by liquid and to preferably exclude or render difficult a complete and permanent wetting.

The invention solves this task with the features indicated hereinafter. Advantageous embodiments of the concept of the invention are indicated below. The form of the filter support of the invention, its channels and the connection conduits to the gas area of the liquid reservoir prevent the channels from becoming filled with liquid if the cannister-shaped filtration device with the enclosed liquid and the integral gas filter is cautiously tilted, as is customary in a working environment, e.g. to evenly mix the cannister contents. If, however, liquid has penetrated to the level of the hydrophobic membrane under extreme conditions or, as a result of awkward handling of the filter device, the pumping movement under changing pressures of the reciprocable membrane between its two filter supports empties the channels of the lower filter support, so that venting and aeration are assured even under extreme conditions.

The concept of the invention is explained in more detail below in two embodiments with reference made to the drawings.

DETAILED DESCRIPTION OF THE INVENTION

Figure 1:
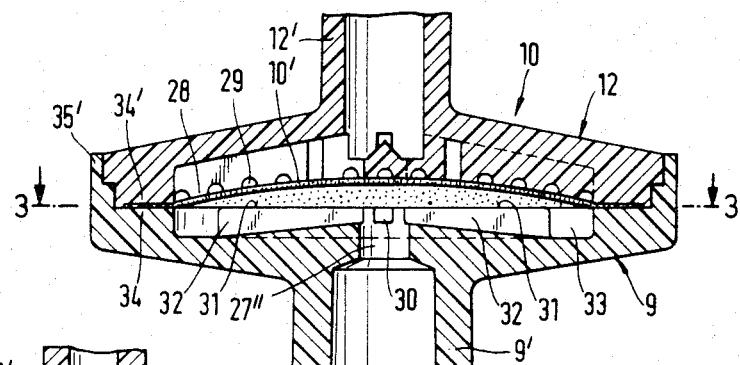
FIG. 1 is a cross-sectional view through a three component filter taken along line 1—1 of FIG. 3.

In accordance with FIG. 1 the device 10 includes an upper disc dome shaped housing part 12 with gas inlet-outlet 12' consists of a one-piece moulded plastic part whose side facing the filter membrane disc 10' has a plurality of radial ribs 28 which form the actual filter support and provide a plurality of spaces 29 connected to an inlet-outlet 12'. Ribs 28, which supports flat filter disc 10', has a concavity in relation to a planar level and the self-contained surface of the lower filter support 31 of mating lower housing part 9 or 6 (of the second embodiment), so that flat filter disc 10', which is clamped in a sandwich-like manner between annular surfaces 34, 34' of the two housing parts 12, 9 or 6 (of the second embodiment) can move axially between both filter supports, 31 and ribs 28. Thus, flat filter disc 10' can execute a kind of pumping movement between both filter supports 28, 31 as a function of the changing pressure conditions. Both housing parts 12, 9 and 12, 6 (of the second embodiment) are connected to one another in a leakproof manner on their periphery on an annular flange 35' or 35 (of the second embodiment) by adhesion or ultra-sound welding.

Figure 2:
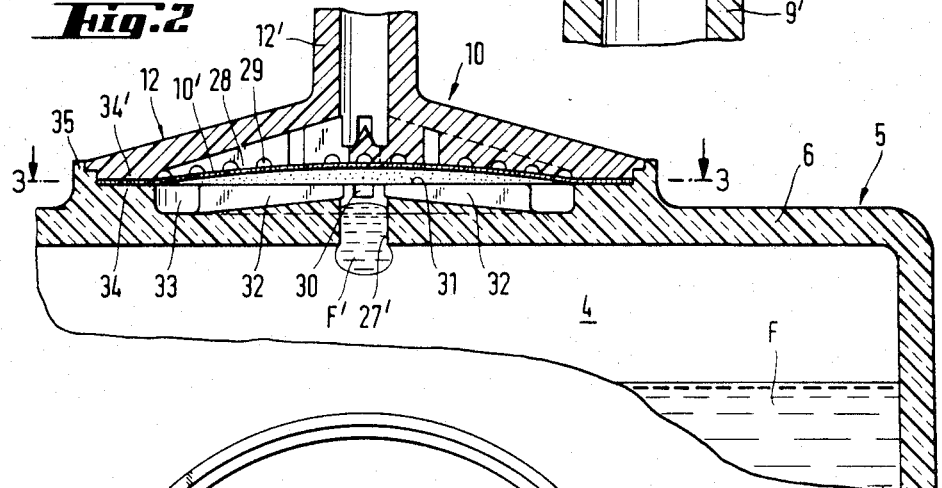
FIG. 2 is a cross-sectional view through another embodiment of the three component filter taken along line 2—2 of FIG. 3.
Figure 4:
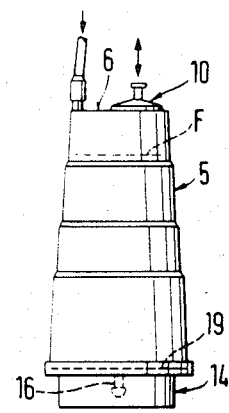
FIG. 4 is a side view of a filter housing in accordance with FIG. 2 embodiment showing the positioning of the filter of the present invention.

Lower housing part 9 in FIG. 1 and housing cover 6 of cannister-shaped filter device 5 in accordance with FIGS. 2, 4 have a small concentric bore 27" and 27' in upper housing part 12 of both embodiments. They are dimensioned as a function of the viscosity of the liquid F in liquid reservoir, for instance, in such a manner that only a relatively small drop F' of liquid can fill up the bore 27" and 27', as is depicted in FIG. 2, if any splashes reach housing cover 6 of the cannister or gets into piece 9' as a result of agitation of the liquid F. If liquid F is an aqueous infusion solution, then the diameter of these bores 27' and 27" is preferably 2 mm with a total length of 2 mm.

Figure 3:
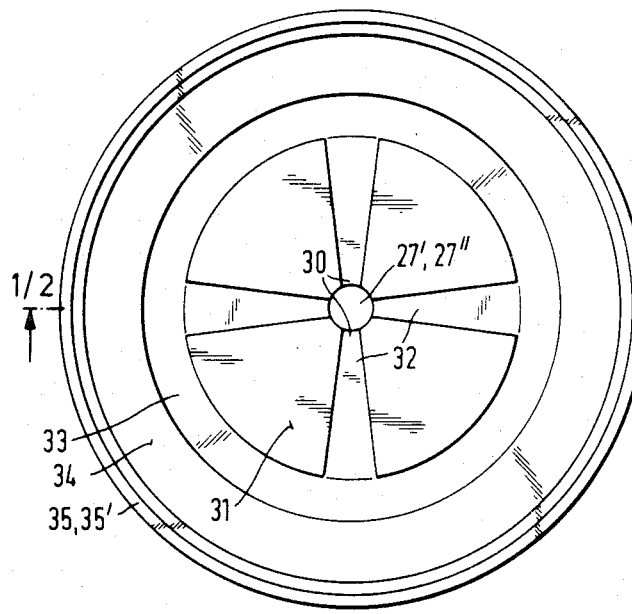
FIG. 3 is a top plan view of the filter with the upper two components removed.

The actual filter support 31 forms a planar, even surface and is interrupted by an annular collector channel 33 proximate the area of the periphery of flat filter blank 10' and by at least one radially extending channel 32 which establishes the connection between annular channel 33 and bores 27' or 27" with the collector channel 33. As FIG. 3 shows, filter support 31 is interrupted by four radially extending channels 32 which divide filter support 31 into four pie-like segments.

Bores 27', 27" end for all practical purposes at the entrance 30 of the radically extending channels 32, which widen out radially, starting from approximately 1 mm said entrance 30, to between about 3 to 10 mm at annular collector channel 33 and is a function of the filter disc diameter. If the total diameter of the filter disc is 25 mm, the radically extending channel drops in the direction of annular collector channel 33 from 0.5 mm to 1.3 mm. The parameters are also related to the viscosity of an aqueous solution.

In the area of bores 27', 27" the radially extending channel 32 has a depth of approximately 0.3 to 0.8 mm, preferably 5 mm, i.e. below the plane of the filter support and increases in depth in the direction of annular collector channel 33 down to 1.1 to 1.6 mm, preferably 1.3 mm. At a diameter of 25 mm the annular collector channel 33 is at least 2 mm wide and 1.3 mm deep. Entrance 30 of the radially extending channels, which communicate into bores 27', 27", is narrower than the opening of bores 27', 27" in this area and is narrower than the diameter (dependent on the viscosity) of a drop F' of liquid from the liquid reservoir. In other words, it will be seen that the apexes of the pie-like segments extend somewhat into the said entrance area 30. The peak of concavity of the curved filter support 28 of upper housing part 12 is located approximately 0.5 to 2 mm over flat filter disc 10', when it rests on lower filter support 31, and in the peripheral edge area upper filter support 28 is located only 0.1 mm to 0.2 mm over the plane of flat filter blank 10'.

In FIGS. 1 and 2 flat filter disc 10' is shown as contacting the upper filter support. This instance occurs when the gas pressure in the lower housing part and/or in gas-liquid reservoir 4 in accordance with FIG. 2 is greater than the gas pressure in inlet/outlet 12' or in the surrounding atmosphere. Such a state occurs, for example, if large filter cannister 5 according to FIGS. 2, 4 is put under pressure with inlet/outlet 12' closed, in order to force liquid F as rapidly as possible through hydrophilic membrane 19 located in the bottom 14 of the cannister 4. In contrast, flat filter disc 10' comes into abutment with lower planar filter support 31 when liquid F is sucked through filter membrane 19 by a vacuum source connected to housing bottom 14 at outlet 16 with the inlet/outlet 12' open to the atmosphere.

If one or several drops F' should actually penetrate into channels 32, 33, then drop F' of liquid is divided at the entrance 30 and is distributed in radially extending channels 32 and annular channel 33 without the entire surface of flat filter disc 10' being wetted.

Thus, sections of flat filter disc 10' in the area of the channels 32 and 33 and also in the area of the actual planar filter support 31 remain relatively free of liquid, so that the hydrophobic filter membrane 10' is usable even under extreme conditions.

We claim:

1. In a filter constructed of an upper dome housing and a mated lower housing and a hydrophobic filter disc for gas filtration sandwiched between them, intended in particular for a gas exchange between a container partially filled with liquid and the surrounding atmosphere:
   (a) the upper housing has an integral upper filter support forming upper channels, the upper channels terminate into a gas inlet-outlet located in the upper housing part,
   (b) the mated lower housing has an integral lower filter support forming lower channels, the lower channels terminate into a bore which run approximately perpendicular to the filter support,
   (c) the hydrophobic filter disc is connected at its periphery between the upper and the lower housing parts as a selectively permeable partition, whereby the filter disc contacts the one or the other filter support as a function of the direction of the pressure gradient, the improvement comprising:
   (1) the filter support of the lower housing part has a planar plane and the lower channels include an annular channel at least 2 mm wide in the area of the periphery of the filter disc and include at least one radially extending lower channel fluidly connecting the bore and said annular channel,
   (2) the radially extending lower channel widens out from the vicinity of the bore from between about 0.5 to 2 mm, in the direction of the annular channel to between about 3 to 10 mm,
   (3) in the area of the bore the radially extending channel has a depth of between about 0.3 to 0.8 mm, and becomes deeper in the direction of the annular channel to between about 1.1 mm to 1.6 mm,
   (4) the bore possesses a length of between about 0.5 mm to 3 mm, and has a diameter of between about 0.5 mm to 4 mm, with it being less at the proximate confluence of the filter support than at the distal end of the bore.

2. The filter according to claim 1, wherein the lower annular channel is at least 2 to 4 mm wide.

3. The filter according to claim 2, wherein there are at least two diametrically opposite radially extending lower channels that divide the lower filter support.

4. The filter according to claim 3, wherein the lower filter support is subdivided in at least three radially extending lower channels thereby producing at least three segments.

5. The filter according to claim 4, wherein the upper filter support in the upper housing part is provided with a support plane that is upwardly concaved in relation to the planar lower filter support of the lower housing part with its apex located approximately 0.5 to 1 mm over the flat filter disc when the disc rests on the lower filter support.

6. The filter according to claim 5, wherein the segments of the lower filter support extend radially inwardly for a distance to form a space which is of smaller diameter than the bore.

* * * * *